(12) United States Patent
Landau

(10) Patent No.: US 6,645,170 B2
(45) Date of Patent: Nov. 11, 2003

(54) SIMPLIFIED DISPOSABLE NEEDLE-FREE INJECTION APPARATUS AND METHOD

(75) Inventor: Sergio Landau, Laguna Niguel, CA (US)

(73) Assignee: Bioject Medical Technologies, Inc., Portland, OR (US)

(*) Notice: Subject to any disclaimer, the term of this patent is extended or adjusted under 35 U.S.C. 154(b) by 62 days.

(21) Appl. No.: 09/864,568

(22) Filed: May 23, 2001

(65) Prior Publication Data

US 2002/0123718 A1 Sep. 5, 2002

Related U.S. Application Data

(63) Continuation-in-part of application No. 09/799,787, filed on Mar. 5, 2001, now Pat. No. 6,471,669.

(51) Int. Cl.[7] .......................... A61M 5/30; A61M 5/315
(52) U.S. Cl. .......................................... 604/68; 604/236
(58) Field of Search .............................. 604/68–72, 118, 604/131, 140–141, 143, 167.01–167.03, 207, 218, 232, 246, 249, 236–238

(56) References Cited

U.S. PATENT DOCUMENTS

| | | |
|---|---|---|
| 2,545,017 A | 3/1951 | Billingsley |
| 2,653,602 A | 9/1953 | Smoot |
| 2,667,874 A | 2/1954 | Dickinson, Jr. |
| 2,680,439 A | 6/1954 | Sutermeister |
| 3,110,309 A | 11/1963 | Higgins |
| 3,115,133 A | 12/1963 | Morando |
| 3,292,621 A | 12/1966 | Banker |
| 3,561,443 A | 2/1971 | Banker |
| 3,688,765 A | 9/1972 | Gasaway |
| 3,695,266 A | 10/1972 | Lussier |
| 3,714,943 A | 2/1973 | Yanof et al. |
| 3,853,125 A | 12/1974 | Clark et al. |
| 3,941,128 A * | 3/1976 | Baldwin ................... 604/199 |
| 3,945,379 A | 3/1976 | Pritz et al. |
| 4,059,107 A | 11/1977 | Iriguchi et al. |
| 4,124,024 A | 11/1978 | Schwebel et al. |
| 4,479,801 A * | 10/1984 | Cohen ...................... 604/238 |
| 4,596,556 A | 6/1986 | Morrow et al. |
| 4,680,027 A | 7/1987 | Parsons et al. |
| 4,717,384 A | 1/1988 | Waldeisen |
| 4,790,824 A | 12/1988 | Morrow et al. |
| 4,913,699 A | 4/1990 | Parsons |
| 4,940,460 A | 7/1990 | Casey, I. et al. |
| 5,009,637 A | 4/1991 | Newman et al. |
| 5,024,656 A | 6/1991 | Gasaway et al. |
| 5,383,851 A * | 1/1995 | McKinnon et al. ......... 604/143 |
| 5,503,627 A * | 4/1996 | McKinnon et al. ........... 604/68 |
| 5,730,723 A | 3/1998 | Castellano et al. |
| 5,993,412 A * | 11/1999 | Deily et al. ................ 604/140 |
| 6,096,002 A * | 8/2000 | Landau ...................... 604/143 |
| 6,132,395 A * | 10/2000 | Landau et al. .............. 604/236 |
| 6,210,359 B1 | 4/2001 | Patel et al. |
| 6,224,567 B1 | 5/2001 | Roser |
| 6,264,629 B1 * | 7/2001 | Landau ...................... 604/143 |
| 6,383,168 B1 * | 5/2002 | Landau et al. .............. 604/236 |
| 2001/0004681 A1 * | 6/2001 | Landau ........................ 604/70 |
| 2002/0123717 A1 * | 9/2002 | Landau ........................ 604/70 |

FOREIGN PATENT DOCUMENTS

| | | |
|---|---|---|
| WO | WO00/33899 | 6/2000 |
| WO | WO00/48654 | 8/2000 |

* cited by examiner

*Primary Examiner*—Brian L. Casler
*Assistant Examiner*—Catherine Serke
(74) *Attorney, Agent, or Firm*—Kolisch Hartwell, P.C.

(57) ABSTRACT

One form of the present invention provides a needle-free injection system including the following components: a cartridge for holding liquid drug prior to injection, the cartridge having a rear end and a front end; a plug mounted to the front end of the cartridge, the plug including a channel; a displaceable valve positioned within the channel prior to injection; and a nozzle portion for receiving liquid drug from the glass cartridge for injection, the nozzle portion including an injection orifice and a drug chamber having a valve seat designed to receive the valve to facilitate injection of liquid drug through the injection orifice.

29 Claims, 6 Drawing Sheets

FIG. 4 PRIMED CONDITION

FIG. 5 PRIMED AND READY CONDITION

FIG. 11

SIMPLIFIED DISPOSABLE NEEDLE-FREE INJECTION APPARATUS AND METHOD

CROSS-REFERENCE TO RELATED APPLICATION

This application is a continuation in part of my prior application entitled Disposable Needle-Free Injection Apparatus and Method, filed Mar. 5, 2001, and given Ser. No. 09/799,787 now U.S. Pat. No. 6,471,669.

BACKGROUND OF THE INVENTION

The present invention relates generally to needle-free or needleless injection systems and more specifically to such a system that is particularly well suited for being used a single time and then being disposed.

RELATED TECHNOLOGY

Needle-free systems have been in use for many years. Some such systems have used a pressurized gas to power a hypodermic jet injection. The related technology includes a number of teachings for gas-powered injection devices, including: U.S. Pat. No. 4,596,556 to Morrow, et al.; U.S. Pat. No. 4,913,699 to Parsons; U.S. Pat. No. 5,730,723 to Castellano, et al.; and WIPO publication WO 97/3705 naming Weston and Thornlea as inventors.

It is also known in this art to provide a needle-free injection system having two plungers that are initially spaced adjacent either end of a glass drug storage sleeve, with liquid drug being disposed between the plungers within the sleeve. Such a system also includes a plastic drug storage chamber disposed coaxially with and forwardly of the glass drug storage sleeve. The forward end of the plastic drug chamber terminates in an injection orifice. The plastic drug chamber includes an enlarged portion that permits drug to flow past the forward plunger when that plunger is aligned with the enlarged portion.

In this prior system, axial force is exerted on the rear plunger immediately prior to injection. Because liquid drug is disposed in the space between the plungers, the plungers move in unison in a forward direction until the forward plunger is aligned with the enlarged portion. At that point, the continued forward travel of the rearward plunder forces liquid drug around the forward plunger until all of the drug is disposed in the plastic drug chamber forward of both plungers, which are now in abutment. The unit thus is ready for actuation. When this prior unit was actuated, the plungers both exerted a forward axial force, causing liquid drug to be directed out of the injection orifice and into the patient.

The invention described in my earlier application, referenced above, is similar to the present invention except that the prior invention, which is not prior art, included more parts and therefore would likely be more expensive to fabricate. This may be more than a theoretical drawback, given that in many applications the user may need to purchase units in quantity because each unit is normally designed to be used only one time prior to disposal.

SUMMARY OF THE INVENTION

One form of the present invention provides a needle-free injection system including the following components: a cartridge for holding liquid drug prior to injection, the cartridge having a rear end and a front end; a plug mounted to the front end of the cartridge, the plug including a channel; a displaceable valve positioned within the channel prior to injection; and a nozzle portion for receiving liquid drug from the glass cartridge for injection, the nozzle portion including an injection orifice and a drug chamber having a valve seat designed to receive the valve to facilitate injection of liquid drug through the injection orifice.

Another aspect of the invention provides a needle free injector with the following components: a housing for holding various injector components; a gas cartridge mounted in the housing for providing a source of pressurized gas; a mechanism for piercing the gas cartridge upon demand, the mechanism being mounted in the housing such that it is moveable with respect to the gas cartridge; a drug cartridge mounted in the housing for storing liquid drug prior to injection; the drug cartridge having a plunger initially positioned at a rearward portion thereof; an injection orifice defined in a front end of the housing and having a fluid inter connection with the drug cartridge; a gas piston for converting gas pressure from the gas cartridge into a forward force exerted on the plunger; and a seal system mounted in the housing for preventing pressurized gas leaving the pierced gas cartridge from reaching the gas piston prior to injection.

A third aspect of the invention provides a method for filling a cartridge with liquid drug for use in a needle-free injection device. The method includes the following steps: providing a plug with a front and a rear and having a rearwardly extending portion and a central channel; positioning a valve in the central channel at a point set back from the front of the plug; providing a cylindrical glass drug cartridge having a front and a rear; positioning a plunger in the rear end of the cartridge; filling the cartridge with liquid drug; and inserting the plug with the valve disposed therein in the front end of the cartridge, and simultaneously having the rearwardly extending portion displace some of the liquid drug in the cartridge so that the liquid drug enters the channel, displacing the valve forwardly within the channel.

BRIEF DESCRIPTION OF THE DRAWINGS

FIGS. 12–16 are a series of schematic views showing how the glass cartridge may be filled with liquid drug prior to assemble of the injector; more specifically.

DETAILED DESCRIPTION OF THE PREFERRED EMBODIMENT

The objects of the invention are best achieved when the invention takes the form of the embodiment depicted in the figures. FIGS. 1–10 depict a first embodiment of the apparatus that is designated generally with the numeral 10. FIGS. 1–8 depict three basic components of the preferred embodiment 10—a nozzle portion 12, a body portion 14 and a trigger portion 16. Nozzle portions 12, body portion 14 and trigger portion 16 combine to form a housing for apparatus 10. These portions will be individually discussed as this description continues.

Figures 1, 8:
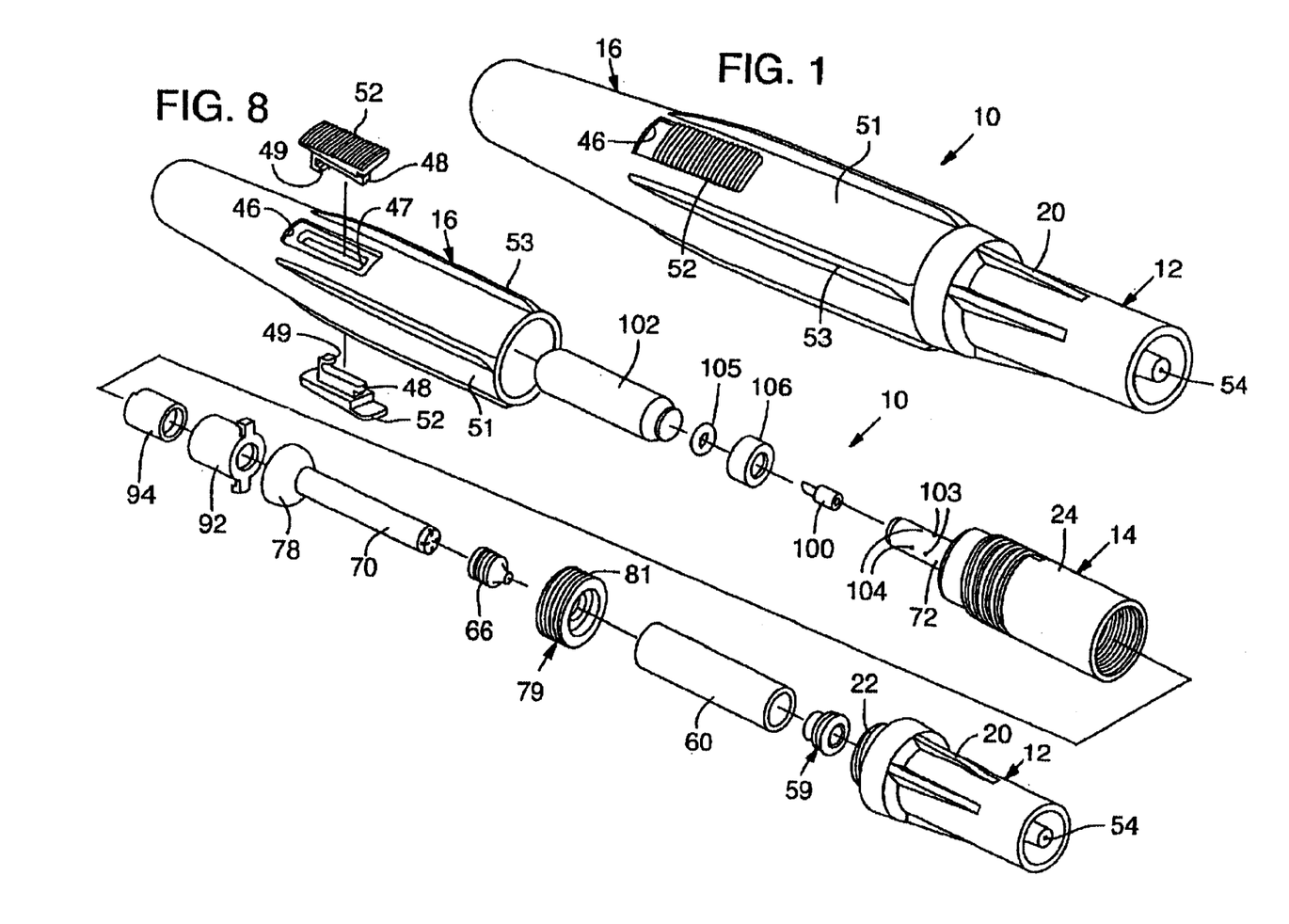
FIG. 1 is an isometric view of a first embodiment of the present invention, showing the unit after it has been fired.
FIG. 8 is an exploded view of the first embodiment of the present invention.
Figure 2:
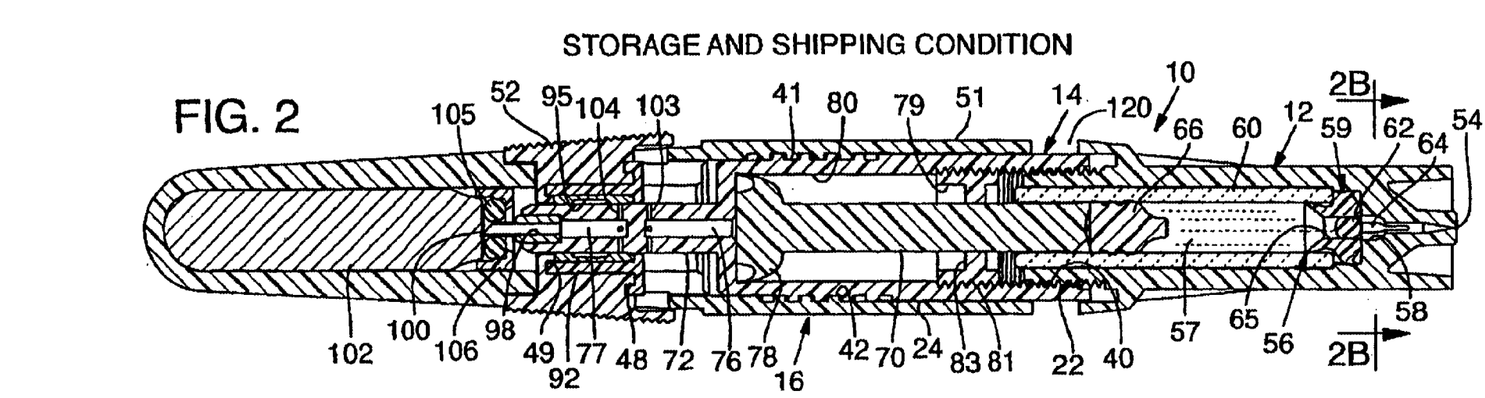
FIG. 2 is a side elevation sectional view of the first embodiment.
Figure 2A:
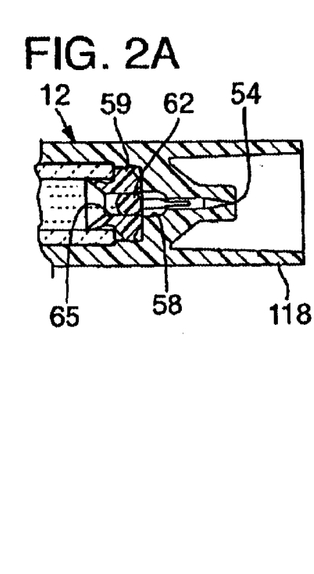
FIG. 2A is a fragmentary side elevation sectional view of the front end of the nozzle portion of a second embodiment of the present invention designed for intradermal injections.
Figures 2B, 3:
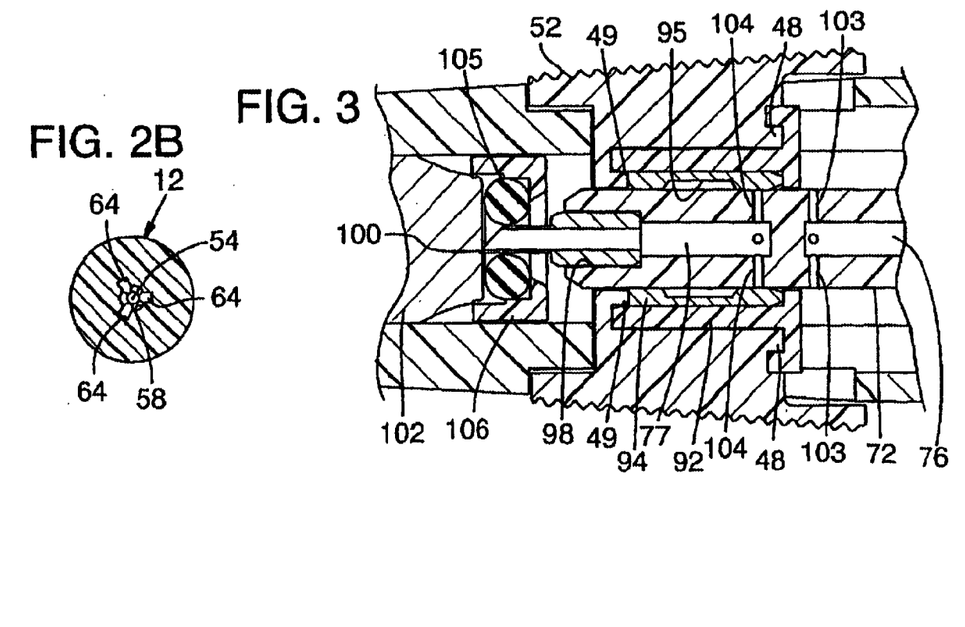
FIG. 2B is an end elevation sectional view taken along line 2B—2B of FIG. 2, showing the bypass conduits in the plastic drug chamber.
FIG. 3 is a side elevation sectional view corresponding to FIG. 2 except that the view is fragmentary and enlarged, showing the preferred gas flow channels and piercing pin position prior to piercing the gas cartridge.

Reference should first be made to FIGS. 2 and 3, which depict apparatus 10 as it is packaged, shipped and received by the customer. The customer in this case may be a clinic, a physician or even a patient. Nozzle portion 12 includes outwardly facing threads 22 that are received in body portion 14, as will be explained in a moment. The nozzle portion 12 also includes strengthening ribs 20.

Body portion 14 includes a forwardly-positioned body 24 and a series of interior threads 40 in the forward portion thereof, designed to receive nozzle portion threads 22. Exterior threads 41 are provided on the body rearwardly of the interior threads to facilitate the body being mounted to trigger portion 16, as will be explained below. Body portion 14 also includes a rearward portion of reduced outer diameter, referred to herein as a gas pressure conduit 72.

Trigger portion 16 extends over body portion 14 and includes interior threads 42 designed to engage body portion threads 41 when apparatus 10 is assembled. Trigger portion 16 also includes strengthening ribs 53 and a pair of undercut portions 46 designed to receive a pair of trigger members 52. A pair of trigger slots 47 permit engagement portions of trigger members 52 to extend therethrough to engage interior components of apparatus 10. The configuration of trigger member engagement portions and the interior components will be described below.

Beginning now at the forward end of apparatus 10, and referring primarily to FIG. 2, the various parts will now be described in more detail. The forward end of nozzle section 12 terminates in an injection orifice 54. The injection orifice provides the means by which liquid drug exits apparatus 10 in a defined, high pressure stream directed into the patient.

A liquid drug chamber is depicted generally at 56, and includes a plastic drug chamber 58 defined by the inwardly facing wall of nozzle portion 12, and a drug storage chamber 57 defined by a glass cartridge 60. Glass cartridge 60 retains the liquid drug during storage and shipment, prior to the point that apparatus 10 is converted to its primed mode. As shown best in FIG. 2B, defined in the walls of plastic drug chamber 58 at the forward end thereof, are three drug bypass conduits 64, evenly spaced around the periphery at 120° increments. While three drug bypass conduits are shown, any number of conduits can be utilized. However many conduits are included, they should be symmetrically positioned around the periphery of plastic drug chamber 58.

Figure 4:
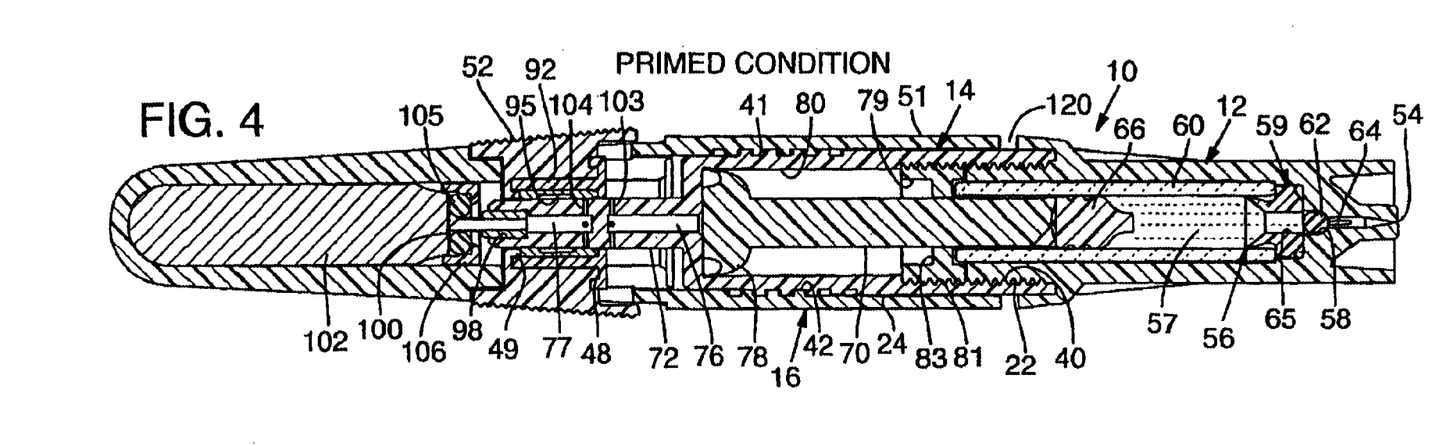
FIG. 4 is a side elevation sectional view corresponding to FIG. 2 except that the first embodiment is shown to be in its primed condition, but prior to the gas cartridge being pierced.
Figure 5:
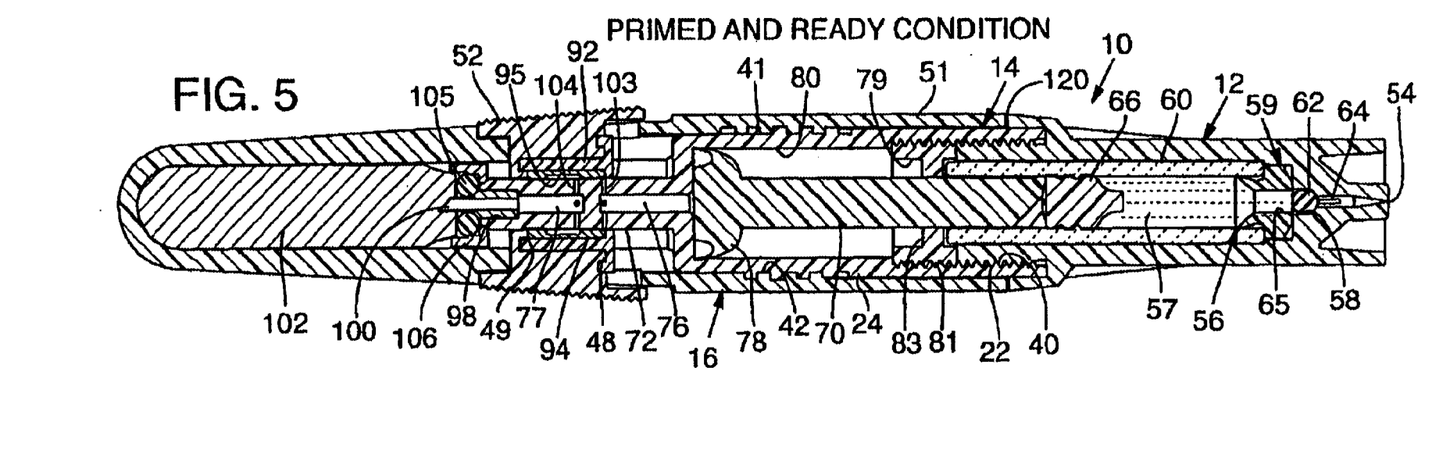
FIG. 5 is a side elevation sectional view corresponding to FIGS. 2, 3 and 4 except that the first embodiment is shown to be in its primed and ready condition, after the gas cartridge has been pierced.
Figure 6:
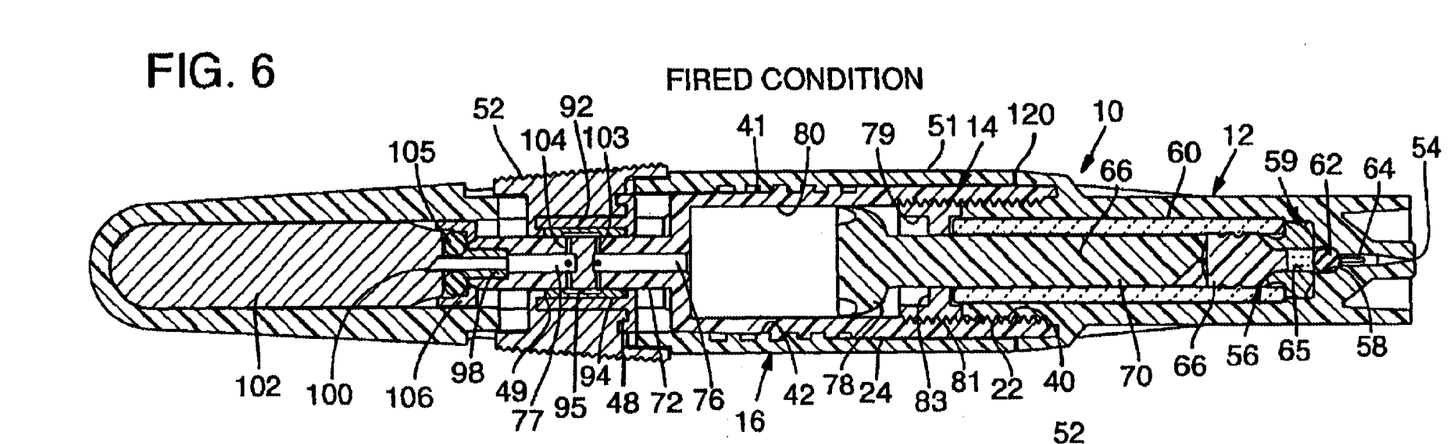
FIG. 6 is a side elevation sectional view corresponding to FIGS. 2, 3, 4 and 5 except that the first embodiment is shown immediately after injection.

Bypass conduits 64 include axially-extending portions that extend along the length of plastic drug chamber 58. These portions are shown in section in FIG. 2B. Bypass conduits 64 also include generally radially-extending portions, which follow the narrowing of the plastic drug chamber. FIGS. 4, 5 and 6 all show a plastic ball valve 62 in its forward position within plastic drug chamber 58. The portions of the inward facing nozzle wall extending between bypass conduits 64 can be seen to support ball valve 62 from the sides and from the front (see also FIGS. 2, 4, 5 and 6).

Positioned immediately to the rear of the plastic drug chamber is a plastic plug 59. The plastic plug is normally fabricated of Teflon, and is used to step down the diameter of glass cartridge 60. Plastic plug 59 fits tightly into the forward end of glass cartridge 60 and also fits tightly into the forward end of the nozzle portion 12. The fit between plastic plug 59 and glass cartridge 60 is shown best in FIG. 9, and the fit of the plastic plug into the forward end of the nozzle portion 12 is shown best in FIG. 10. Plastic plug 59 includes a body 61 that exerts a rearward force on the cartridge, a rearwardly extending flared portion 63 that exerts an outward force on the interior walls of the cartridge, and a plug channel 65 that extends through the center of the plug. The diameter of plug channel 65 is slightly smaller than that of ball valve 62 so that the ball valve stays in place in the channel unless pressure acts on it to displace it in a forward direction. Ball valve 62 is typically fabricated of Teflon, although it may be formed of butyl rubber or a similar material.

Figure 11:
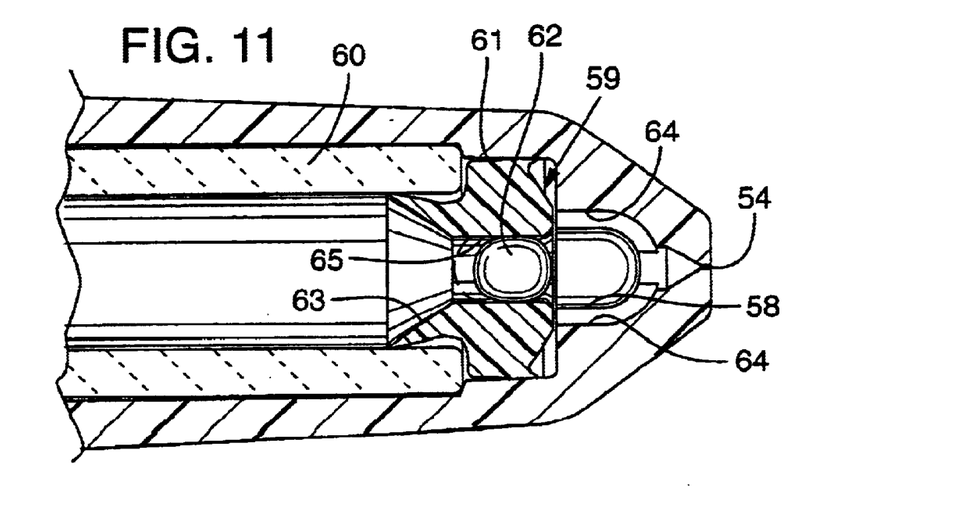
FIG. 11 is an enlarged, side elevation sectional view corresponding to FIG. 10 except that an alternate embodiment of the nozzle portion is shown.

FIG. 11 shows a ball valve 62 that is identical to ball valve 62 of the other figures but the depicted nozzle portion 112 is of slightly different design.

Referring again to FIGS. 1–10, glass cartridge 60 is shown to be of cylindrical configuration. This is preferable to a narrowed bottle-like configuration of some prior designs because it is easier and therefore less expensive to fabricate. The drawback with some prior systems that included cylindrical designs is that the plastic drug chamber of those prior systems ends up being much wider in cross-section than is needed. In fact, the wider cross-section is a drawback in that a larger area needs to be filled with liquid drug before injection can take place. The use of a plastic plug 59 combines the inexpensive fabrication advantages of a cylindrical glass cartridge and the small plastic drug chamber advantages of a bottle-shaped glass cartridge.

As mentioned previously, liquid drug chamber 56 includes a plastic drug chamber 58 and a glass drug storage chamber 57. The forward end of glass drug storage chamber 57 is defined by plastic plug 59 and ball valve 62. The rearward end of glass drug storage chamber 57 is defined by a drug plunger 66. Drug plunger 66 is fabricated of a relatively impermeable elastomer material, such as butyl rubber, which is also inert so that there is no chemical or biological reaction to the drug. Drug plunger 66 fits tightly into the glass cartridge so that the drug plunger maintains its position with respect to glass cartridge 60 unless it is forced in a forward directly by a gas piston 70, disposed immediately rearwardly thereof. Gas piston 70 is positioned along the longitudinal center line of apparatus 10 in directly alignment with drug plunger 66 and ball valve 62. Gas piston 70 extends rearwardly or to the left in the figures, and includes a rearwardly extending cupped portion 78 facing rearwardly in a concave figuration. Cupped portion 78 of gas piston 70 fits tightly against an inner diameter 80 of body portion 14. If fluid pressure is exerted in a rightward or forward direction, cupped portion 78 pushes even more forcefully against inner diameter 80 so that leakage past the cup portion is prevented. Configuration of gas piston 70 therefore facilitates a conversion of fluid pressure exerted from the rear of the gas piston to a forward force exerted on drug plunger 66. This facilitates injection of liquid drug into a patient as will be understood as this discussion continues.

As described earlier, body portion 14 is one of the three basic components of apparatus 10. FIG. 2 shows nozzle threads 22 only partially engaged in body threads 40, this condition is maintained when apparatus 10 is in its storage or shipping condition. When nozzle portion 12 is threaded entirely into body portion 14, as shown in FIG. 4, space 120 is reduced in size as nozzle portion 12 butts up against an abutment member 79. Abutment member 79 includes threads 81 which thread into body interior threads 40. When nozzle portion 12 is in abutment with abutment member 79 as shown in FIG. 4, an abutment member flange 83 comes into abutment with the rearward end of glass cartridge 60. This holds glass cartridge 80 in position during the injection process.

Referring again to gas pressure conduit 72 at the rearward end of body portion 14, it can be seen that an axially extending gas pressure channel extends through the center of the gas pressure conduit. This gas pressure channel is divided into two axially spaced channels 76 and 77. A plurality of radially-extending gas pressure channels 103 are positioned at the rearward end of the forward gas pressure channel 76. In the depicted embodiment, four angularly spaced, radially-extending gas pressure channels 103 are included, but it may be desirable in certain applications to have more or fewer such channels. For example, in certain applications it may be possible to have only one such channel. On some applications, where there are multiple channels, they may be referred to as radial gas conduits. Four radially-extending gas pressure channels 104 are also included in the forward end of the rearward gas pressure channel 77, although, again, more or fewer such channels may be provided.

A piercing pin receiving seat 98 is positioned at the rearward end of the rearward gas pressure channel 77 and this seat is designed to hold a hollow piercing pin 100. The piercing pin will sometimes be called a piercing mechanism. Piercing pin 100 is in position adjacent the front end of a gas cartridge 102. Gas pressure cartridge 102 typically includes Nitrogen ($N_2$) gas to provide gas pressure for the injection process. An O ring 105 is provided adjacent to the forward end of gas cartridge 102, and a cap 106 is positioned to hold O ring 105 in place.

The third of the three major components of apparatus 10 is trigger portion 16. It includes a long extension member 51, which extends forwardly to nozzle portion 12. Extension member 51 includes a plurality of axially extending ribs 53 designed to strengthen apparatus 10 and provide a gripping surface for the user.

As mention previously, a pair of trigger members 52 are positioned in undercut portions 46 of trigger portion 16. Also included are trigger slots 47 into which engagement portions of the trigger members extend. The engagement portions of trigger members 52 include a forward engagement member 48 and a rearward engagement member 49. Forward engagement member 48 engages a sliding bushing 92 which is pushed forwardly by forward engagement member 48 as each trigger member 52 is slid to its forward position depicted in FIG. 6. Rearward engagement member 49 engages a sealing bushing 94. Sealing bushing 94 is best shown FIG. 3, and includes an annular gap 95 that extends all of the way around gas pressure conduit 72 at the midportion of sealing bushing 94. The function of sealing bushing 94 is to either block or permit flow of gas pressure from forward and rearward radially-extending gas pressure channels 103 and 104 to control the firing of apparatus 10. Thus, for example, with each of the trigger members 52 in its rearward most position as shown in FIGS. 2 and 3, sealing bushing 94 prevents gas under pressure from passing out of rearward radially-extending gas pressure channels 104. When trigger members 52 are slid to their forward-most position, shown in FIG. 6, both the forward and the rearward radially-extending gas pressure channels 103 and 104 are uncovered by sealing bushing 94 and are exposed to annular gap 95. As shown by the flow lines in FIG. 7, this permits gas under pressure to flow from rearward gas pressure channel 76, out rearward radially-extending gas pressure channels 104, forwardly through annular gap 95 and into forward radially-extending gas pressure channels 103 and forward gas pressure channel 77. This permits gas to flow forwardly through forward gas pressure channel 77 to facilitate the injection process, as will be more fully explained below.

Filling the Preferred Embodiment with Liquid Drug

Figure 12:
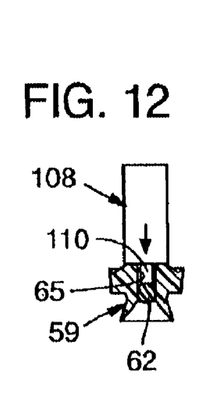
FIG. 12 is a side elevation view showing a ball valve being initially positioned in the rearward end of the plastic plug.

FIGS. 12–16 schematically depict the operation in which glass cartridge 60 is filled with liquid drug. FIG. 12 shows the process by which ball valve 62 is inserted into plastic plug 59. A ball positioning tool 108 having an extension member 110 is depicted. The ball is initially positioned at the forward (or upper as depicted) end of plug channel 65, but is then pushed to its rearward-most position within the plug channel by extension member 110.

Figure 13:
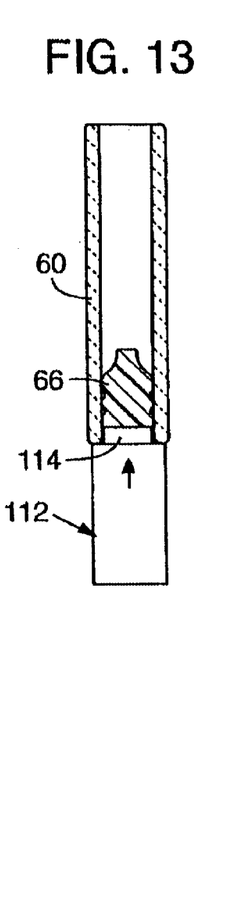
FIG. 13 is a side elevation view showing a drug plunger being positioned in the rearward end of the glass cartridge.
Figure 14:
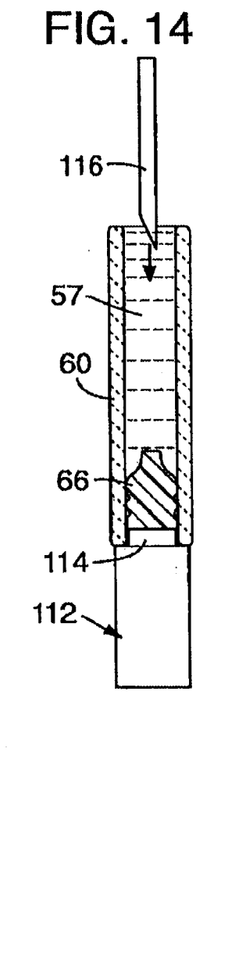
FIG. 14 is a side elevation view showing a liquid drug filling tube having filled the cartridge with liquid drug.

FIGS. 13 and 14 show the positioning of drug plunger 66 in glass cartridge 60, using a drug plunger positioning tool 112 having an extension member 114. The use of drug plunger positioning tool 112 positions the drug plunger at a point only slightly forward (or above as depicted) of the rearward (or bottom) end of glass cartridge 60.

Figure 15:
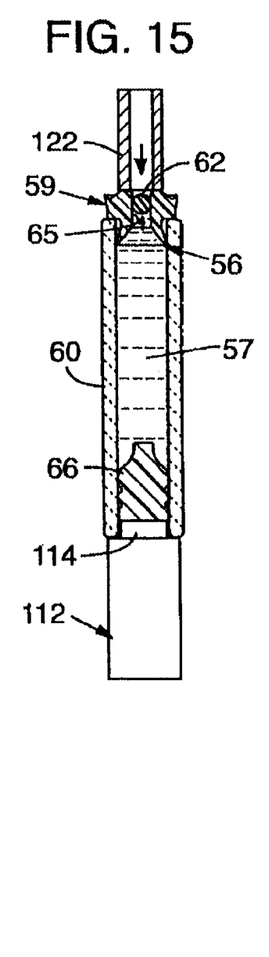
FIG. 15 is a side elevation view showing the plastic plug being pressed into position in the forward end of the glass cartridge which is filled with liquid drug, and depicting how the ball valve is displaced forwardly in the plastic plug during this process.

Once drug plunger 66 has been properly positioned within glass cartridge 60, the glass cartridge is filled with liquid drug as shown in FIG. 14 using a conventional filling tube 116. Once glass cartridge 60 has been filled to the top with liquid drug, plastic plug 59 with ball valve 62 positioned therein is ready for mounting to the glass cartridge. This is shown in FIG. 15. During this process, drug plunger 66 must be held in position, either due to friction, or by keeping drug plunger positioning tool 112 in position as depicted. Plastic plug 59 is pressed onto the forward (or upper) end of glass cartridge 60 using a plug positioning tool 122. As plastic plug 59 is pressed into glass cartridge 60, liquid drug is displaced by flange portion 63 of the plastic plug. This displacement is accommodated by ball valve 62 which shifts from its rearward-most position depicted in FIG. 12, to its forward-most position depicted in FIG. 15.

This system of mounting plastic plug 59 into glass cartridge 60 minimizes the amount of air which is introduced into the liquid drug and reduces the effort that must be made to precisely position the various components during the assembly process. This reduces the cost of assembly which is likely to be passed to the end user in lower costs as well.

With the now-filled glass cartridge being stopped at both ends, glass cartridge 60 can be stored and held for use, or can be mounted into nozzle portion 12, which is the preferred storage mode.

Figure 16:
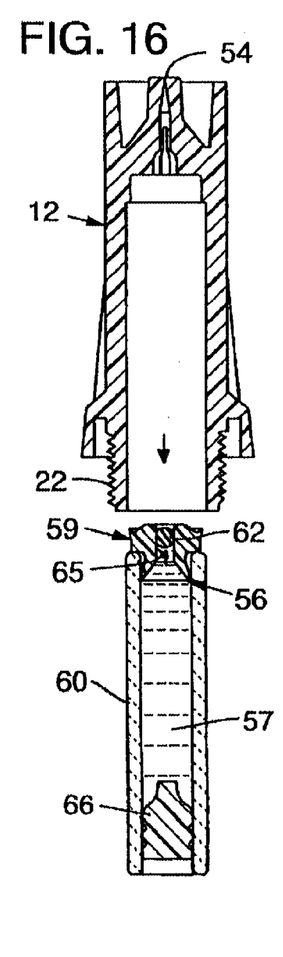
FIG. 16 is a side elevation view showing the glass cartridge filled with liquid drug and with the drug plunger and plastic plug in place, being installed into the nozzle portion of the injector.

FIG. 16 shows the process by which the filled glass cartridge 60 is inserted into nozzle portion 12 of apparatus 10. Because air within nozzle portion 12 will be permitted to pass out injection orifice 54 during this insertion process, ball valve 62 will not be displaced and air will not be introduced into the liquid drug within glass cartridge 60.

Operation of the Preferred Embodiment

At any time after the filled glass cartridge 60 has been installed into nozzle portion 12, assembly of apparatus 10 may be completed. This is performed at the factory and is shown in its assembled condition in FIG. 2. The nozzle portion 12 is shown to be only partially threaded into body portion 14, leaving a large space 120 between nozzle portion 12 and trigger portion 16. Thus, nozzle threads 22 are shown to engage interior body threads 40, but the two portions are not threaded all of the way into one another. In this storage condition, ball valve 62 is shown to be positioned as it was at the end of the filling process depicted in FIGS. 15 and 16. That is, it is within plug channel 65, adjacent the forward end thereof. In this storage condition, trigger members 52 are in their rearward position, so sealing bushing 94 covers the rear radially-extending gas pressure channels 104, as best shown in FIG. 3. In this storage configuration, piercing pin 100 is shown to be adjacent to the forward end of gas cartridge 102, but the gas cartridge is not yet pierced and the apparatus is not yet primed.

After apparatus 10 has been shipped to the end user, normally the patient, and the patient is ready for an injection, the patient threads nozzle portion 12 all of the way into body portion 14. As seen in FIG. 4, this substantially reduces space 120 and causes ball valve 62 to shift forwardly into plastic drug chamber 58, and liquid drug flows through bypass conduits 64 and around ball valve 62 to remove any air in the front of plastic drug chamber 58. Liquid drug within glass cartridge 60 is pushed forwardly during the process of threading nozzle portion 12 all of the way into body portion 14 because drug plunger 66 is held stationary by gas piston 70 as the nozzle portion is threaded toward the body portion. Once nozzle portion 12 has been threaded all the way into body portion 14, the rearward end of the nozzle portion comes into contact with abutment member 79. A small amount of liquid drug may dribble out of injection orifice 54, but this is necessary to ensure that all of the air has been removed from nozzle portion 12. Apparatus 10 is now primed, but it is not yet ready for injection.

To complete the preparation process, body portion 14 is threaded all of the way into trigger portion 16 as exterior threads 41 in body 24 are threaded into trigger interior threads 42. This final threading process causes piercing pin 100 to pierce gas cartridge 102. This primed and ready condition is shown in FIG. 5. However, injection is not yet effected, because trigger members 52 remain in their rearward position. In this condition, pressurized $N_2$ gas passes from gas cartridge 102, through piercing pin 100 and into rearward axial gas pressure channel 77 and rearward radial gas pressure channels 104. Pressure is blocked from reaching forward radial gas pressure channels 103 by sealing busing 94 which now covers forward radial gas pressure channels 103.

Figure 7:
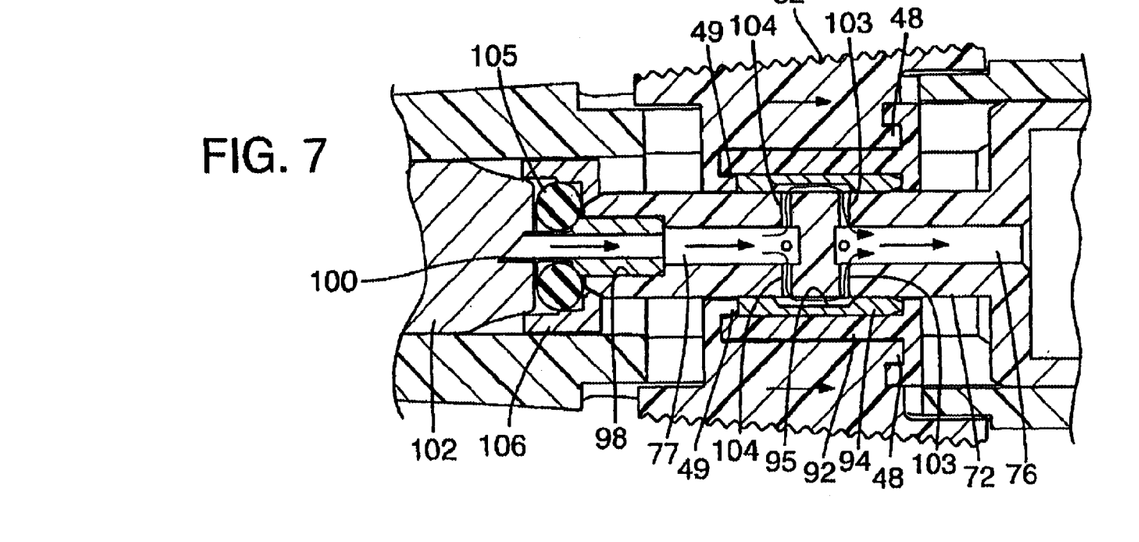
FIG. 7 is a side elevation sectional view corresponding to FIG. 6 except that the view is fragmentary and enlarged, showing the preferred mechanism for controlling the flow of gas under pressure from the gas cartridge to the forward portion of the injector, showing gas pressure being conveyed to the forward portion of the injector.
Figure 9:
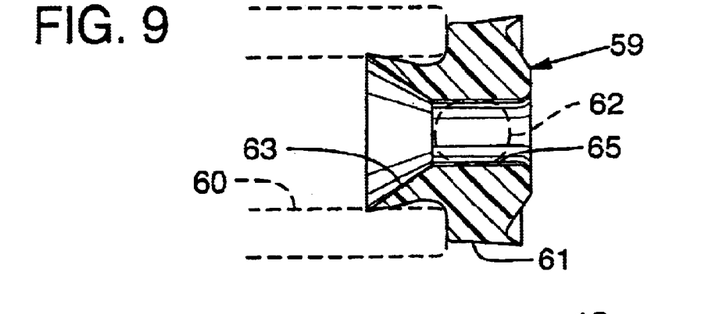
FIG. 9 is an enlarged, side elevation sectional view of a plastic plug disposed in the forward portion of the first embodiment of the present invention, showing how the plug fits into the forward end of a glass cartridge (which is shown in phantom)
Figure 10:
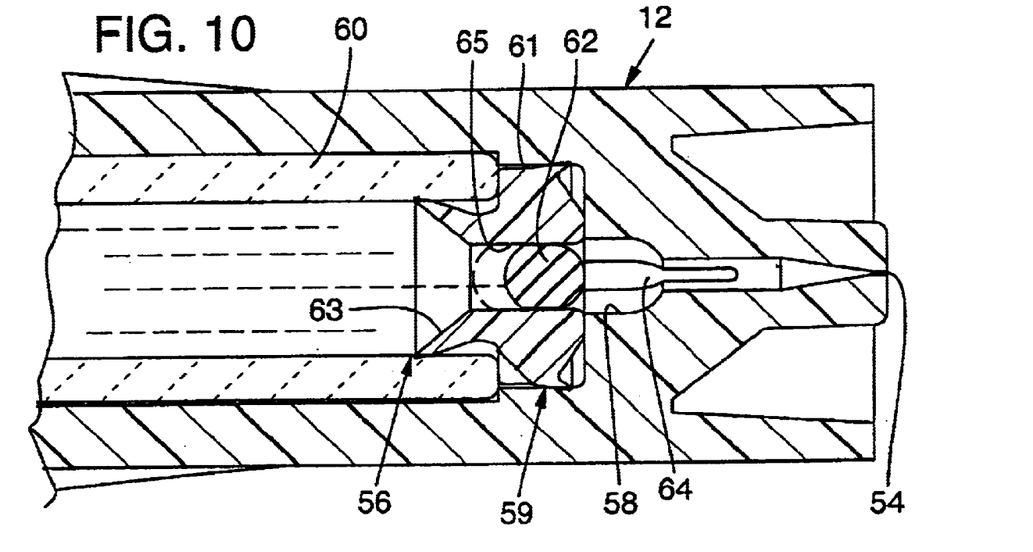
FIG. 10 is an enlarged, side elevation sectional view of the first embodiment showing how the plastic plug and glass cartridge fit into the forward or nozzle portion of the injector.

In order to effect injection, the patient simply positions the forward end of injection orifice 54 against the body part to be injected. With one hand, the patient can then shift trigger members 52 to the forward position depicted in FIG. 6. The forward engagement member pushes sliding bushing 92 forwardly or to the right as shown in the figures. Rearward engagement member 49 pushes sealing bushing 94 forwardly to the position shown in FIGS. 6 and 7. This permits gas to flow under pressure from gas cartridge 102 through piercing pin 100 and rearward gas pressure channel 77, out rearward radially-extending gas pressure channels 104, across annular gap 95 and back into forward radially-extending gas pressure channels 103 and then forwardly through forward gas pressure gas channel 76 all as shown in FIG. 7. Gas under pressure then enters the interior of body 24, pushing cupped portion 78 of gas piston 70 forwardly or to the right in FIG. 6. This forward force forces cupped portion 78 outwardly, to provide an effective seal between the cup portion and inner diameter 80 of body 24. Gas piston 70 is thus driven forwardly, pushing drug plunger 66 to the right, and causing liquid drug to flow around ball valve 62 via bypass conduits 64 and out injection orifice 54 and into the patient.

This system thus provides an effective and simple injection which may be performed by the patient using a single hand. This is accomplished using far fewer parts than prior systems. Because this results in the apparatus relatively inexpensive, it is designed for single use and can be disposed after firing.

Variations can be made to the depicted embodiment without departing from the scope of the invention, and the following claims are intended to cover such variations.

I claim:

1. A needle-free injection system comprising:
   a cylindrical cartridge for holding liquid drug prior to injection, the cartridge having a rear end and a front end;
   a plug mounted to and having a portion positioned forward of the front end of the cartridge, the plug defining a narrowed throat and including a channel;
   a displaceable valve positioned within the channel prior to injection; and
   a nozzle portion for receiving liquid drug from the glass cartridge for injection, the nozzle portion including an injection orifice and a drug chamber having a valve seat designed to receive the valve to facilitate injection of liquid drug through the injection orifice.

2. The system of claim 1 wherein bypass conduits are defined between the drug chamber and the valve to facilitate flow of liquid drug around the valve during injection.

3. The system of claim 2 wherein the bypass conduits are defined in the drug chamber and the valve is spherical in configuration.

4. The system of either of claim 2 or 3, further comprising a plunger disposed initially at a rearward end of the cartridge, the plunger being forwardly displaceable to push the valve forwardly from the plug channel to the valve seat and then to force liquid drug through the channel, the bypass conduits and the injection orifice.

5. The system of claim 1 wherein the cartridge is glass and the plug, drug chamber and valve are plastic.

6. A needle-free injection system comprising:
a cartridge for holding liquid drug prior to injection, the cartridge having a rear end and a front end;
a plug mounted to the front end of the cartridge, the plug including a channel and a body and a flange that extends rearwardly into the cartridge;
a displaceable valve positioned within the channel prior to injection; and
a nozzle portion for receiving liquid drug from the glass cartridge for injection, the nozzle portion including an injection orifice and a drug chamber having a valve seat designed to receive the valve to facilitate injection of liquid drug through the injection orifice.

7. The system of claim 6 wherein the plug fits tightly against the cartridge, with the body exerting a rearward force on the cartridge and the flange exerting an outward force on an interior surface of the cartridge.

8. A needle-free injection system comprising:
a cylindrical glass cartridge for holding liquid drug prior to injection, the cartridge having a rear end and a front end and a longitudinal axis;
a nozzle portion defining an injection orifice at a front end thereof for injecting liquid drug received from the glass cartridge;
a plug mounted to and having a portion positioned forward of the front end of the cartridge, the plug defining a narrowed throat and including a channel in coaxial alignment with the longitudinal axis of the cartridge and the injection orifice, the channel being smaller in dimension than the cartridge; and
a displaceable valve positioned within the channel prior to injection.

9. The system of claim 8 wherein the plug and the valve are fabricated of plastic.

10. The system of claim 8 wherein the valve is spherical in configuration.

11. The system of claim 8 wherein the nozzle portion further comprises a plastic drug chamber disposed between the plug and the injection orifice, for receiving the valve immediately prior to injection.

12. The system of claim 11 wherein bypass conduits are defined between the plastic drug chamber and the valve so that liquid drug flows through the bypass conduits and then out the injection orifice during injection.

13. The system of claim 12 wherein the bypass conduits are defined in the plastic drug chamber and the valve is spherical in configuration.

14. The system of claim 12 wherein the bypass conduits include axially- and radially-extending portions.

15. A needle-free injection system comprising:
a cylindrical glass cartridge for holding liquid drug prior to injection, the cartridge having a rear end and a front end and a longitudinal axis;
a nozzle portion defining an injection orifice at a front end thereof for injecting liquid drug received from the glass cartridge;
a plug mounted to the front end of the cartridge, the plug including a channel in coaxial alignment with the longitudinal axis of the cartridge and the injection orifice, the channel being smaller in dimension than the cartridge;
wherein the plug fits tightly against the cartridge and the plug includes a body that exerts a rearward force on the cartridge and includes a flange that extends rearwardly into the cartridge, exerting an outward force on an interior surface of the cartridge; and
a displaceable valve positioned within the channel prior to injection.

16. The system of claim 15, further comprising an axially displaceable plunger positioned initially in a rear portion of the glass cartridge.

17. The system of claim 16, further comprising a mechanism for selectively applying axial force to the plunger to drive it forwardly to effect injection.

18. The system of claim 15, further comprising a body portion, and the nozzle portion and body portion include complementing threads for coupling the nozzle portion and body portion together, and wherein rotating the nozzle portion and the body portion relative to each other assists in preparing the system for injection.

19. The system of claim 18, further comprising a trigger portion that is threaded to threadably couple to one or both of the nozzle portion and body portion, and wherein rotating the trigger portion relative to one or both of the nozzle portion and the body portion assists in preparing the system for injection.

20. The system of claim 18, further comprising a trigger portion having a gas cartridge therein, the trigger portion being threaded to threadably couple to the body portion, and wherein rotating the nozzle portion and the body portion relative to each other primes the system, and rotating the trigger portion and the body portion relative to each other pierces the gas cartridge.

21. The system of claim 20, further comprising a trigger disposed in the trigger portion, and actuation of the trigger permits pressurized gas to flow forwardly in the system to force liquid drug from the glass cartridge and out the injection orifice.

22. A needle-free injector comprising:
a housing for holding various injector components;
a gas cartridge mounted in the housing for providing a source of pressurized gas;
a mechanism for piercing the gas cartridge upon demand, the mechanism being mounted in the housing such that it is moveable with respect to the gas cartridge;
a drug cartridge mounted in the housing for storing liquid drug prior to injection, the drug cartridge having a plunger initially positioned at a rearward portion thereof;
an injection orifice defined in a front end of the housing and having a fluid inter connection with the drug cartridge;
a gas piston for converting gas pressure from the gas cartridge into a forward force exerted on the plunger; and
a seal system mounted in the housing for preventing pressurized gas leaving the pierced gas cartridge from reaching the gas piston prior to injection;
wherein the seal system includes a first axial gas channel extending forwardly from the gas cartridge, a first radial gas channel extending radially outwardly from the axial gas channel; and an axially displaceable seal that is displaceable from a first position covering the first radial gas channel to a second position where the first radial gas channel is uncovered.

23. The injector of claim 22 wherein the seal system further includes a second axial gas channel extending forwardly from a point axially offset from the first axial gas channel, and a second radial gas channel extending radially outwardly from the second axial gas channel at a point axially offset from the first radial gas channel.

24. The injector of claim 23 wherein the seal includes a pair of sealing surfaces with a space defined therebetween, and the seal is displaceable between a first position in which at least one of the sealing surfaces is covering at least one of the radial gas channels, and a second position in which the space is disposed over the first and the second radial gas channels.

25. The injector of claim 24 wherein each of the first and second radial gas channels comprises a plurality of angularly offset conduits.

26. The injector of any one of claims 22, 23, 24, or 25, further comprising at least one trigger member that is moveable between two positions, the trigger member being interconnected with the seal so that by moving the trigger member, the seal is moved, thereby controlling the flow of gas pressure from the gas cartridge to the gas piston for exerting forward force on the plunger, thereby driving liquid drug from the drug cartridge, out the injective orifice.

27. The method of claim 26, further comprising:
holding the plunger in position while the plug is inserted into the cartridge.

28. The injector of claim 22 wherein the mechanism for piercing the gas cartridge comprises a hollow pin.

29. A method for filling a cartridge with liquid drug for use in a needle-free injection device, comprising:
providing a plug with a front and a rear and having a rearwardly extending portion and a central channel;
positioning a valve in the central channel at a point set back from the front of the plug;
providing a cylindrical glass drug cartridge having a front and a rear;
positioning a plunger in the rear end of the cartridge;
filling the cartridge with liquid drug; and
inserting the plug with the valve disposed therein in the front end of the cartridge, and simultaneously having the rearwardly extending portion displace some of the liquid drug in the cartridge so that the liquid drug enters the channel, displacing the valve forwardly within the channel.

* * * * *